(12) United States Patent
Porchia et al.

(10) Patent No.: US 7,246,919 B2
(45) Date of Patent: Jul. 24, 2007

(54) LED LIGHT BULB WITH ACTIVE INGREDIENT EMISSION

(75) Inventors: Jose Porchia, Greenfield, WI (US); Jeffrey J. Wolf, Racine, WI (US)

(73) Assignee: S.C. Johnson & Son, Inc., Racine, WI (US)

(*) Notice: Subject to any disclaimer, the term of this patent is extended or adjusted under 35 U.S.C. 154(b) by 93 days.

(21) Appl. No.: 11/069,964

(22) Filed: Mar. 3, 2005

(65) Prior Publication Data

US 2005/0195600 A1 Sep. 8, 2005

Related U.S. Application Data

(60) Provisional application No. 60/549,154, filed on Mar. 3, 2004.

(51) Int. Cl.
*F21V 23/04* (2006.01)

(52) U.S. Cl. ............... 362/276; 362/643; 362/650; 362/253; 392/393

(58) Field of Classification Search ........ 362/640–643, 362/646, 647, 650, 172, 240, 260, 276, 253; 392/393; 422/227, 234
See application file for complete search history.

(56) References Cited

U.S. PATENT DOCUMENTS

| | | |
|---|---|---|
| 1,535,486 A | 4/1925 | Lundy |
| 1,565,500 A | 12/1925 | Ritter |
| 1,706,939 A | 3/1929 | Rosenthal |
| 1,732,707 A | 10/1929 | Winsboro |
| 1,920,599 A | 8/1933 | Schuh |
| 2,124,543 A | 7/1938 | Clyne |
| 2,143,246 A | 1/1939 | McGary |
| 2,372,371 A | 3/1945 | Eisner |
| 2,435,756 A | 2/1948 | Schlesinger |
| 2,468,164 A | 4/1949 | Brewster |
| 2,469,656 A | 5/1949 | Lienert |
| 2,535,802 A | 12/1950 | Libson |
| 2,579,026 A | 12/1951 | Walter |
| 2,694,771 A | 11/1954 | Cox |
| 2,741,812 A | 4/1956 | Tellier |
| 2,741,813 A | 4/1956 | Rubin |
| 2,799,166 A | 7/1957 | Leftwich |
| 2,818,770 A | 1/1958 | Cilurzo |
| 2,931,880 A | 4/1960 | Yaffe |
| 2,942,090 A | 6/1960 | Diehl |

(Continued)

FOREIGN PATENT DOCUMENTS

GB 2 239 306 6/1991

(Continued)

*Primary Examiner*—Renee Luebke
*Assistant Examiner*—Evan Dzierzynski
(74) *Attorney, Agent, or Firm*—Miller, Matthias & Hull

(57) ABSTRACT

A light bulb (10) includes a translucent housing (12) and a base (24). The housing (12) includes a plurality of LEDs (14a, 14b, 14c, and 15) positioned so as to emit light through the housing (12). The base (24) is configured to mate with a light socket. The base (24) also includes a compartment (23) for receiving and securing a replaceable active ingredient cartridge (22), and an active ingredient dispenser (20) for emitting an active ingredient from the cartridge (22) when the cartridge (22) is secured in the compartment (23). A fluorescent light source (30) may also be provided in the housing (12) as a source of illumination.

20 Claims, 5 Drawing Sheets

U.S. PATENT DOCUMENTS

| | | |
|---|---|---|
| 3,080,624 A | 3/1963 | Weber, III |
| 3,119,565 A | 1/1964 | Nottingham |
| 3,377,126 A | 4/1968 | Nijland et al. |
| 3,760,179 A | 9/1973 | Addington, Jr. |
| 3,763,347 A | 10/1973 | Whitaker |
| 3,780,260 A | 12/1973 | Elsner |
| 3,923,458 A | 12/1975 | Moran |
| 3,948,445 A | 4/1976 | Andeweg |
| 4,009,384 A | 2/1977 | Holland |
| 4,045,664 A | 8/1977 | Vrenken et al. |
| 4,084,079 A | 4/1978 | Costello |
| 4,184,099 A | 1/1980 | Lindauer et al. |
| 4,234,907 A | 11/1980 | Daniel |
| 4,271,408 A | 6/1981 | Teshima |
| 4,346,059 A | 8/1982 | Spector |
| 4,391,781 A | 7/1983 | van Lit |
| 4,463,286 A | 7/1984 | Justice |
| 4,493,011 A | 1/1985 | Spector |
| 4,510,555 A | 4/1985 | Mori |
| 4,519,017 A | 5/1985 | Daniel |
| 4,544,592 A | 10/1985 | Spector |
| 4,549,250 A | 10/1985 | Spector |
| 4,561,043 A | 12/1985 | Thompson |
| 4,579,717 A | 4/1986 | Gyulay |
| 4,631,387 A | 12/1986 | Glucksman |
| 4,640,266 A | 2/1987 | Levy |
| 4,647,428 A | 3/1987 | Gyulay |
| 4,647,433 A | 3/1987 | Spector |
| 4,714,984 A | 12/1987 | Spector |
| 4,754,372 A | 6/1988 | Harrison |
| 4,816,973 A | 3/1989 | Atalla et al. |
| 4,849,181 A | 7/1989 | Kelley et al. |
| 4,849,606 A | 7/1989 | Martens, III et al. |
| 4,875,144 A | 10/1989 | Wainwright |
| 4,885,663 A | 12/1989 | Parker |
| 4,933,815 A | 6/1990 | Parthasarathy |
| 4,955,975 A | 9/1990 | Mori |
| 4,965,490 A * | 10/1990 | Ratner ................. 313/569 |
| 4,965,701 A | 10/1990 | Voland |
| 4,972,305 A | 11/1990 | Blackburn |
| 4,974,136 A | 11/1990 | Noori-Shad et al. |
| 5,021,928 A | 6/1991 | Daniel |
| 5,046,837 A | 9/1991 | Stroomer et al. |
| 5,060,118 A | 10/1991 | Penrod et al. |
| 5,066,085 A | 11/1991 | Gimbutas et al. |
| 5,069,877 A | 12/1991 | Pozzo |
| 5,111,477 A | 5/1992 | Muderlak |
| 5,133,042 A | 7/1992 | Pelonis |
| 5,168,654 A | 12/1992 | Chien |
| 5,178,839 A | 1/1993 | Spector |
| 5,183,323 A | 2/1993 | Daniel |
| 5,201,025 A | 4/1993 | Landesberg |
| 5,217,696 A | 6/1993 | Wolverton et al. |
| 5,233,680 A | 8/1993 | Fussell |
| 5,247,491 A | 9/1993 | Kwiatkowski |
| 5,249,105 A | 9/1993 | Koizumi |
| 5,251,116 A | 10/1993 | Wijbenga et al. |
| 5,259,062 A | 11/1993 | Pelonis |
| 5,301,090 A | 4/1994 | Hed |
| D350,209 S | 8/1994 | Martin |
| 5,345,149 A | 9/1994 | Ham |
| 5,352,122 A | 10/1994 | Speyer et al. |
| 5,374,876 A | 12/1994 | Horibata et al. |
| 5,402,517 A | 3/1995 | Gillett et al. |
| D357,330 S | 4/1995 | Wong et al. |
| 5,426,474 A | 6/1995 | Rubtsov et al. |
| 5,432,876 A | 7/1995 | Appeldorn et al. |
| D363,537 S | 10/1995 | Moody |
| 5,455,750 A | 10/1995 | Davis et al. |
| 5,463,280 A | 10/1995 | Johnson |
| 5,547,616 A | 8/1996 | Dancs et al. |
| 5,556,191 A | 9/1996 | Maassen |
| 5,556,192 A | 9/1996 | Wang |
| 5,561,346 A | 10/1996 | Byrne |
| 5,568,964 A | 10/1996 | Parker et al. |
| 5,598,068 A | 1/1997 | Shirai |
| D381,443 S | 7/1997 | Yuen |
| D381,444 S | 7/1997 | Yuen |
| 5,647,052 A | 7/1997 | Patel et al. |
| 5,651,942 A | 7/1997 | Christensen |
| 5,688,042 A | 11/1997 | Madadi et al. |
| 5,691,886 A | 11/1997 | Stacy |
| 5,703,440 A | 12/1997 | Kachmarik et al. |
| 5,711,591 A | 1/1998 | Jordan |
| 5,726,535 A | 3/1998 | Yan |
| D395,529 S | 6/1998 | Yuen |
| 5,801,484 A | 9/1998 | Bankuti et al. |
| 5,823,652 A | 10/1998 | Vann |
| 5,876,678 A | 3/1999 | Harrell et al. |
| 5,908,231 A | 6/1999 | Huff |
| 6,016,038 A | 1/2000 | Mueller et al. |
| 6,031,967 A | 2/2000 | Flashinski et al. |
| 6,044,202 A | 3/2000 | Junkel |
| 6,099,137 A | 8/2000 | McCormack et al. |
| 6,106,786 A | 8/2000 | Akahoshi |
| 6,120,737 A | 9/2000 | Zembrodt |
| D433,521 S | 11/2000 | Jaworski |
| 6,143,313 A | 11/2000 | Ito et al. |
| 6,148,143 A | 11/2000 | Steinel, Jr. |
| 6,149,283 A | 11/2000 | Conway et al. |
| 6,150,774 A | 11/2000 | Mueller et al. |
| 6,153,980 A | 11/2000 | Marshall et al. |
| 6,154,607 A | 11/2000 | Flashinski et al. |
| 6,166,496 A | 12/2000 | Lys et al. |
| 6,183,100 B1 | 2/2001 | Suckow et al. |
| 6,200,002 B1 | 3/2001 | Marshall et al. |
| 6,211,626 B1 | 4/2001 | Lys et al. |
| 6,217,188 B1 | 4/2001 | Wainwright et al. |
| 6,220,722 B1 | 4/2001 | Begemann |
| 6,220,742 B1 | 4/2001 | Lloyd et al. |
| 6,234,645 B1 | 5/2001 | Borner et al. |
| 6,234,648 B1 | 5/2001 | Borner et al. |
| 6,234,649 B1 | 5/2001 | Katougi |
| 6,239,716 B1 | 5/2001 | Pross et al. |
| 6,254,248 B1 | 7/2001 | McAuley et al. |
| 6,270,720 B1 | 8/2001 | Mandish |
| 6,289,176 B1 | 9/2001 | Martter et al. |
| 6,292,901 B1 | 9/2001 | Lys et al. |
| 6,294,800 B1 | 9/2001 | Duggal et al. |
| 6,299,338 B1 | 10/2001 | Levinson et al. |
| 6,302,559 B1 | 10/2001 | Warren |
| 6,318,876 B1 | 11/2001 | Sigro et al. |
| 6,337,080 B1 | 1/2002 | Fryan et al. |
| 6,339,298 B1 | 1/2002 | Chen |
| 6,340,868 B1 | 1/2002 | Lys et al. |
| 6,357,889 B1 | 3/2002 | Duggal et al. |
| 6,371,450 B1 | 4/2002 | Davis et al. |
| 6,371,634 B1 | 4/2002 | Tufte |
| D457,667 S | 5/2002 | Piepgras et al. |
| D457,669 S | 5/2002 | Piepgras et al. |
| D457,974 S | 5/2002 | Piepgras et al. |
| 6,391,329 B1 | 5/2002 | Ito et al. |
| 6,392,549 B1 | 5/2002 | Wu |
| D458,395 S | 6/2002 | Piepgras et al. |
| 6,398,381 B1 | 6/2002 | Tseng |
| 6,400,104 B1 | 6/2002 | Ham |
| 6,402,347 B1 | 6/2002 | Maas et al. |
| 6,406,172 B1 | 6/2002 | Harbers et al. |
| D460,573 S | 7/2002 | Gee, II |
| 6,413,476 B1 | 7/2002 | Barnhart |
| 6,416,180 B1 | 7/2002 | Strobl |
| D463,610 S | 9/2002 | Piepgras et al. |
| 6,459,919 B1 | 10/2002 | Lys et al. |
| 6,472,876 B1 | 10/2002 | Notohamiprodjo et al. |

| | | | | | | | |
|---|---|---|---|---|---|---|---|
| 6,478,440 | B1 * | 11/2002 | Jaworski et al. ............... 362/96 | 6,869,202 | B2 | 3/2005 | Tufte |
| 6,478,453 | B2 | 11/2002 | Lammers et al. | 6,869,204 | B2 | 3/2005 | Morgan et al. |
| 6,480,649 | B2 | 11/2002 | Lee | 6,874,909 | B2 | 4/2005 | Vanderschuit |
| 6,482,863 | B2 | 11/2002 | Munagavalasa et al. | 6,880,948 | B2 | 4/2005 | Koch et al. |
| D468,035 | S | 12/2002 | Blanc et al. | 6,883,929 | B2 | 4/2005 | Dowling |
| 6,488,393 | B1 | 12/2002 | Burnham | 6,883,931 | B2 | 4/2005 | Tufte |
| 6,499,860 | B2 | 12/2002 | Begemann | 6,888,322 | B2 | 5/2005 | Dowling et al. |
| 6,503,459 | B1 | 1/2003 | Leonard et al. | 6,890,085 | B2 | 5/2005 | Hacker |
| 6,513,954 | B2 | 2/2003 | Ebersole | 6,897,624 | B2 | 5/2005 | Lys et al. |
| 6,528,954 | B1 | 3/2003 | Lys et al. | 6,902,301 | B2 | 6/2005 | Kieronski |
| 6,536,910 | B2 | 3/2003 | Lin | 6,921,184 | B2 | 7/2005 | Tufte |
| 6,536,914 | B2 | 3/2003 | Hoelen et al. | 6,936,978 | B2 | 8/2005 | Morgan et al. |
| 6,539,656 | B2 | 4/2003 | Maas et al. | 6,951,401 | B2 | 10/2005 | Van Hees et al. |
| 6,543,925 | B2 | 4/2003 | Kuykendal et al. | 6,952,079 | B2 | 10/2005 | Shiang et al. |
| 6,547,416 | B2 | 4/2003 | Pashley et al. | 6,957,897 | B1 | 10/2005 | Nelson et al. |
| 6,547,423 | B2 | 4/2003 | Marshall et al. | 6,965,205 | B2 | 11/2005 | Piepgras et al. |
| 6,548,967 | B1 | 4/2003 | Dowling et al. | 6,966,665 | B2 | 11/2005 | Limburg et al. |
| 6,551,560 | B1 | 4/2003 | Flashinski et al. | 6,976,774 | B2 | 12/2005 | Reiss |
| 6,558,022 | B2 | 5/2003 | Kawahara | 7,008,096 | B1 | 3/2006 | Coushaine et al. |
| 6,573,536 | B1 | 6/2003 | Dry | 7,038,399 | B2 | 5/2006 | Lys et al. |
| 6,577,080 | B2 | 6/2003 | Lys et al. | 7,052,152 | B2 | 5/2006 | Harbers et al. |
| 6,586,882 | B1 | 7/2003 | Harbers | 7,067,981 | B2 | 6/2006 | Nishio et al. |
| 6,601,982 | B1 | 8/2003 | Begemann et al. | 7,075,224 | B2 | 7/2006 | Coushaine |
| 6,608,453 | B2 | 8/2003 | Morgan et al. | 7,080,932 | B2 | 7/2006 | Keuper |
| 6,613,288 | B2 | 9/2003 | Gupte | 7,086,756 | B2 | 8/2006 | Maxik |
| 6,624,597 | B2 | 9/2003 | Dowling et al. | 7,086,767 | B2 | 8/2006 | Sidwell et al. |
| 6,626,554 | B2 * | 9/2003 | Rincover et al. ........... 362/186 | 7,093,958 | B2 | 8/2006 | Coushaine |
| 6,627,857 | B1 | 9/2003 | Tanner et al. | 7,104,679 | B2 | 9/2006 | Shin et al. |
| 6,628,885 | B1 | 9/2003 | Wilkie et al. | 7,109,665 | B2 | 9/2006 | Green |
| 6,629,772 | B2 | 10/2003 | Brunfeld | 7,116,294 | B2 | 10/2006 | Stopa |
| 6,636,003 | B2 | 10/2003 | Rahm et al. | 7,160,012 | B2 | 1/2007 | Hilscher et al. |
| 6,642,669 | B1 | 11/2003 | MacAdam et al. | 7,175,302 | B2 | 2/2007 | Kazer et al. |
| 6,648,486 | B2 | 11/2003 | Harbers et al. | 2001/0014019 | A1 | 8/2001 | Begemann |
| 6,648,496 | B1 | 11/2003 | Elghoroury et al. | 2001/0035853 | A1 | 11/2001 | Hoelen et al. |
| 6,655,824 | B2 | 12/2003 | Tufte | 2001/0038532 | A1 | 11/2001 | Harbers et al. |
| 6,672,734 | B2 | 1/2004 | Lammers | 2002/0006044 | A1 | 1/2002 | Harbers et al. |
| 6,676,282 | B2 | 1/2004 | Begemann et al. | 2002/0030997 | A1 | 3/2002 | Tufte |
| 6,688,753 | B2 * | 2/2004 | Calon et al. ................ 362/236 | 2002/0071285 | A1 | 6/2002 | Tufte |
| 6,712,494 | B1 | 3/2004 | Hodge | 2002/0075671 | A1 | 6/2002 | Tufte |
| 6,717,376 | B2 | 4/2004 | Lys et al. | 2002/0075674 | A1 | 6/2002 | Tufte |
| 6,720,745 | B2 | 4/2004 | Lys et al. | 2002/0075677 | A1 | 6/2002 | Dokoupil |
| 6,726,341 | B2 | 4/2004 | Pashley et al. | 2002/0075679 | A1 | 6/2002 | Machi et al. |
| 6,733,161 | B2 | 5/2004 | Tufte | 2002/0105800 | A1 | 8/2002 | Tufte |
| D491,678 | S | 6/2004 | Piepgras et al. | 2002/0118538 | A1 | 8/2002 | Calon et al. |
| D492,042 | S | 6/2004 | Piepgras et al. | 2002/0131273 | A1 | 9/2002 | Tufte |
| 6,742,914 | B2 | 6/2004 | Prodell | 2002/0135997 | A1 | 9/2002 | Lammers |
| 6,745,506 | B2 | 6/2004 | Maas et al. | 2002/0141058 | A1 | 10/2002 | Itoh |
| 6,758,573 | B1 | 7/2004 | Thomas et al. | 2002/0145392 | A1 | 10/2002 | Hair, III et al. |
| 6,774,584 | B2 | 8/2004 | Lys et al. | 2003/0007887 | A1 | 1/2003 | Roumpos et al. |
| 6,777,891 | B2 | 8/2004 | Lys et al. | 2003/0021117 | A1 * | 1/2003 | Chan ......................... 362/260 |
| 6,779,905 | B1 * | 8/2004 | Mazursky et al. .......... 362/101 | 2003/0039115 | A1 | 2/2003 | Lin |
| 6,781,329 | B2 | 8/2004 | Mueller et al. | 2003/0046842 | A1 | 3/2003 | Maas et al. |
| 6,783,117 | B2 * | 8/2004 | Wohrle ........................ 261/26 | 2003/0071932 | A1 | 4/2003 | Tanigaki |
| 6,788,011 | B2 | 9/2004 | Mueller et al. | 2003/0078791 | A1 | 4/2003 | Tufte |
| 6,793,360 | B2 | 9/2004 | Goslee | 2003/0095409 | A1 | 5/2003 | Cheng |
| 6,796,685 | B1 | 9/2004 | Nemirow | 2003/0096535 | A1 | 5/2003 | Miller, Jr. |
| 6,801,003 | B2 | 10/2004 | Schanberger et al. | 2003/0102810 | A1 | 6/2003 | Cross et al. |
| 6,802,635 | B2 | 10/2004 | Robertson et al. | 2003/0117088 | A1 | 6/2003 | Tanabe et al. |
| 6,806,659 | B1 | 10/2004 | Mueller et al. | 2003/0137258 | A1 | 7/2003 | Piepgras et al. |
| 6,815,724 | B2 | 11/2004 | Dry | 2003/0156425 | A1 | 8/2003 | Turnbull et al. |
| 6,817,731 | B2 | 11/2004 | Tufte | 2003/0209183 | A1 | 11/2003 | Tufte |
| 6,831,303 | B2 | 12/2004 | Dry | 2003/0231488 | A1 | 12/2003 | Albee |
| 6,833,539 | B1 | 12/2004 | Maeda | 2004/0066652 | A1 * | 4/2004 | Hong ......................... 362/234 |
| 6,837,591 | B2 | 1/2005 | Tufte | 2004/0070967 | A1 | 4/2004 | Kennedy |
| 6,840,646 | B2 | 1/2005 | Cornelissen et al. | 2004/0080941 | A1 | 4/2004 | Jiang et al. |
| 6,844,824 | B2 | 1/2005 | Vukosic | 2004/0095078 | A1 | 5/2004 | Leong |
| 6,848,822 | B2 | 2/2005 | Ballen et al. | 2004/0095754 | A1 | 5/2004 | Hsu |
| 6,851,844 | B2 | 2/2005 | Guy | 2004/0095780 | A1 | 5/2004 | Reed |
| 6,854,208 | B1 | 2/2005 | Chuang et al. | 2004/0109317 | A1 | 6/2004 | Ribarich |
| 6,854,854 | B2 | 2/2005 | Hoelen et al. | 2004/0124790 | A1 | 7/2004 | Han et al. |
| 6,854,869 | B1 | 2/2005 | Fernandez | 2004/0135522 | A1 | 7/2004 | Berman et al. |
| 6,858,994 | B2 | 2/2005 | Vollrath | 2004/0189218 | A1 | 9/2004 | Leong et al. |
| D503,467 | S | 3/2005 | Flashinski et al. | 2004/0189262 | A1 | 9/2004 | McGrath |

| | | |
|---|---|---|
| 2004/0246711 A1 | 12/2004 | Brenchley et al. |
| 2004/0257798 A1 | 12/2004 | Hart et al. |
| 2004/0264185 A1 | 12/2004 | Grotsch et al. |
| 2005/0024892 A1 | 2/2005 | Cabrera |
| 2005/0030747 A1 | 2/2005 | Bogdal |
| 2005/0036300 A1 * | 2/2005 | Dowling et al. ............ 362/101 |
| 2005/0047127 A1 | 3/2005 | Tutman |
| 2005/0074358 A1 | 4/2005 | Hart et al. |
| 2005/0099108 A1 | 5/2005 | Hofmann et al. |
| 2005/0104503 A1 | 5/2005 | Ellens et al. |
| 2005/0128751 A1 | 6/2005 | Roberge et al. |
| 2005/0169015 A1 | 8/2005 | Luk et al. |
| 2005/0169666 A1 | 8/2005 | Porchia et al. |
| 2005/0173675 A1 | 8/2005 | Schmidt et al. |
| 2005/0185392 A1 | 8/2005 | Walter et al. |
| 2005/0195600 A1 | 9/2005 | Porchia et al. |
| 2005/0258439 A1 | 11/2005 | Dry |
| 2005/0258440 A1 | 11/2005 | Dry |
| 2005/0259416 A1 | 11/2005 | Gauna et al. |
| 2005/0265018 A1 | 12/2005 | Yasuda et al. |
| 2005/0265023 A1 | 12/2005 | Scholl |
| 2005/0269581 A1 | 12/2005 | Dry |
| 2005/0275626 A1 | 12/2005 | Mueller et al. |
| 2005/0281030 A1 | 12/2005 | Leong et al. |
| 2005/0285538 A1 | 12/2005 | Jaworski et al. |
| 2006/0001677 A1 | 1/2006 | Webb et al. |
| 2006/0002102 A1 | 1/2006 | Leonard |
| 2006/0002110 A1 | 1/2006 | Dowling et al. |
| 2006/0006784 A1 | 1/2006 | Takahara et al. |
| 2006/0022214 A1 | 2/2006 | Morgan et al. |
| 2006/0023447 A1 | 2/2006 | Justel et al. |
| 2006/0045818 A1 | 3/2006 | Moreland |
| 2006/0055315 A1 | 3/2006 | Bokor et al. |
| 2006/0071589 A1 | 4/2006 | Radkov |
| 2006/0081871 A1 | 4/2006 | Streubel |
| 2006/0082333 A1 | 4/2006 | Laski |
| 2006/0083013 A1 | 4/2006 | Wanninger et al. |
| 2006/0103291 A1 | 5/2006 | Ellens et al. |
| 2006/0114670 A1 | 6/2006 | Ho |
| 2006/0120080 A1 | 6/2006 | Sipinski et al. |
| 2006/0158138 A1 * | 7/2006 | Walter et al. ............... 315/316 |
| 2006/0176690 A1 | 8/2006 | Yuen |
| 2006/0220990 A1 | 10/2006 | Coushaine et al. |
| 2006/0238136 A1 | 10/2006 | Johnson, III et al. |
| 2006/0275040 A1 | 12/2006 | Franklin |

FOREIGN PATENT DOCUMENTS

| | | |
|---|---|---|
| JP | 2002/186660 | 2/2002 |
| JP | 2002/159980 | 6/2002 |
| JP | 2003/310732 | 5/2003 |
| WO | WO 99/57945 | 11/1999 |
| WO | WO 01/78488 A2 | 10/2001 |
| WO | WO 03/013618 | 2/2003 |
| WO | WO 03/026358 | 3/2003 |
| WO | WO 03/098971 | 11/2003 |
| WO | WO 2004/068945 A1 | 8/2004 |
| WO | WO 2004/073399 A1 | 9/2004 |
| WO | WO 05/003625 | 1/2005 |

* cited by examiner

LED LIGHT BULB WITH ACTIVE INGREDIENT EMISSION

BACKGROUND OF THE INVENTION

Creating a pleasant ambience is a popular aspect of home decor. This is often achieved through pleasant fragrances and proper lighting. Conventional products such as scented candles, mood lighting devices, fragrance dispensers, and the like, are commonly used to create a pleasant environment in the home. While those conventional products help to create a pleasant living environment and ambiance, they have their drawbacks.

For example, scented candles create soft light and fragrance, which creates a pleasant mood. However, candles are a potential fire hazard and often produce unwanted smoke and wax drippings.

Traditional light fixtures and lamps do not provide color effects or fragrances users often desire. Other than existing lamps, stand-alone aesthetic devices are available for providing desired lighting effects (such as color changing and the like). However, such devices take up space around the home, and could add to the clutter that many are trying to avoid. Also, because such stand-alone devices are typically placed in highly visible locations, they need to be aesthetically designed to suit the personal tastes of different categories of buyers, requiring additional design costs.

Conventional fragrance dispensers, such as plug-in diffusers, can provide pleasing aromas in a relatively inexpensive, compact package. However, such conventional fragrance dispensers generally take up outlets and are often located out of sight, causing a user to forget to adjust or refill the device. While these fragrance dispensers may also provide light, because the devices are used in existing electrical outlets, they are generally positioned too low to provide effective lighting features, other than to operate as a nightlight.

SUMMARY OF THE INVENTION

In view of the drawbacks of the lighting and fragrance devices currently on the market, we have invented a device which provides the desired lighting and fragrance effects (or emission of other active ingredients, other than fragrance), without adding clutter to a room, requiring the purchase of new fixtures, taking up additional electrical outlets, requiring aesthetically pleasing designs for the unit itself, or presenting the fire hazards associated with open flames. More specifically, our invention is directed to a light bulb that is configured to mate with a light socket (e.g., conventional incandescent, halogen or fluorescent light sockets), and provides the desired ambient effects related to lighting and fragrance.

In one aspect, a light bulb according to our invention includes a translucent housing, a plurality of LEDs positioned within the housing so as to emit light through the housing, a base configured to mate with a light socket, a compartment for receiving and securing a replaceable active ingredient cartridge, and a dispenser for emitting the active ingredient from the cartridge when secured in the compartment.

In another aspect, a light bulb according to our invention includes a base configured to mate with a light socket for receiving the light bulb, a translucent housing coupled to the base, and a plurality of LEDs, including LEDs of at least two different colors, coupled to the base within the housing. An active ingredient dispenser is supported by the base and dispenses an active ingredient from the light bulb when the active ingredient is provided therein. A control mechanism is provided, by which the light bulb can be controlled by a user to change at least one of a color of light emitted from the housing by the plurality of LEDs, and an output rate of the active ingredient.

A light bulb according to our invention may provide white light typically associated with a conventional light bulb, as well as colored options, color-changing effects, and/or fragrance emission. In addition, all of these options may be provided in one simple replacement bulb that can be placed in existing lamps already found in one's home. The light bulb may include a compact fluorescent bulb in the housing for providing illumination/white light. Moreover, it is preferred that the colored lighting effects of our light bulb be provided by light emitting diodes (LEDs), which last longer than conventional bulbs, are more energy efficient, and do not emit the high levels of heat associated with, for example, incandescent bulbs. With this reduction in heat, we have found it is possible to more effectively and efficiently deliver a fragrance (or other active ingredient), without overheating or burning the same. Also, LEDs may be used to provide an additional or alternative source of white light.

In preferred embodiments, the fragrance delivery aspect of our invention may be provided by scented oil or scented gels provided in cartridges which may be replaceably secured in/to the bulb, to provide the desired fragrance emission. This allows a user to change between different fragrances and/or replace empty cartridges, without the need to change the entire bulb. In addition, our bulb can be made programmable so that a user may change the lighting options (i.e., change the brightness or color, or activate a color show), and/or the fragrance emission rate.

DETAILED DESCRIPTION OF THE PREFERRED EMBODIMENTS

Figure 1:
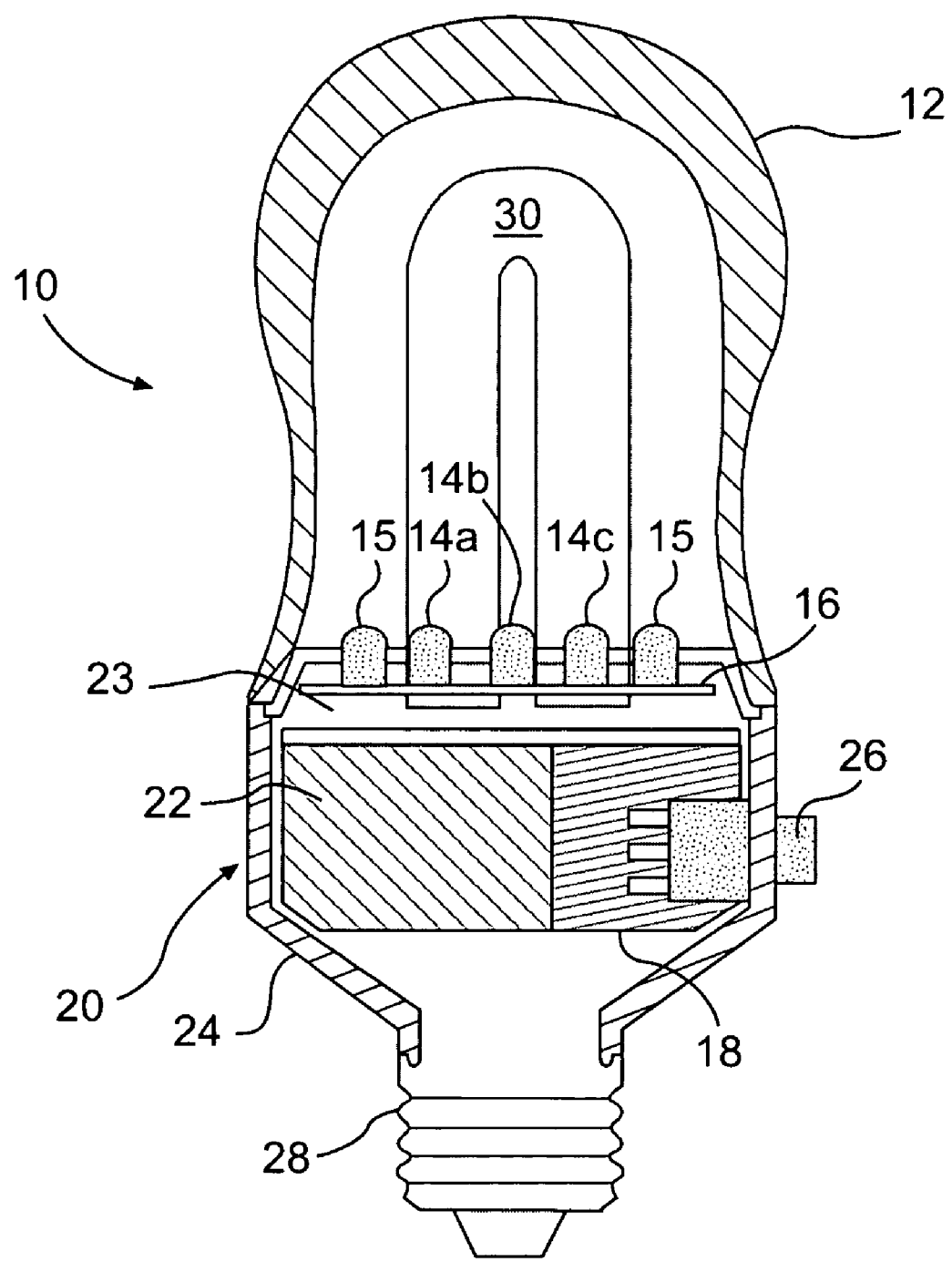
FIG. 1 is a cross-sectional view of a bulb according to our invention with a threaded, screw-in base.

FIG. 1 shows a screw-in bulb 10. While our invention can be embodied in bulbs that mate with any one of a number of lighting fixtures (such as conventional fixtures for receiving incandescent, halogen, or fluorescent bulbs), for exemplary purposes, the description provided herein refers to an Edison-style, screw-in light bulb that mates with a conventional incandescent light socket with a threaded female receptacle. Of course, our invention may be embodied in any light bulb that mates with a light socket/power source.

Bulb 10 includes a translucent housing 12 mounted on a base 24. Connected to the bottom of base 24 is a threaded male, screw-in connector 28, which is configured to mate with a threaded female socket of a conventional lamp or other lighting fixture. When connector 28 is mated with such a socket, AC power is provided to bulb 10 from the lamp or lighting fixture.

The power is provided to an LED board (light array) 16, on which LEDs 14a (red), 14b (green), 14c (blue), and 15 (white) are mounted. These LEDs may be operated in any one of a number of combinations to provide a specific color of light, color shows or patterns that are pleasing to a user. For example, the LEDs may be operated as described in International Publication No. WO2005/003625, which is incorporated herein by reference. Housing 12 may act as a light diffuser, to cause a user to perceive the intended color, rather than the activation of distinct LEDs of different colors. Alternatively, a separate diffuser may be provided inside the housing 12. The diffuser operates to combine the lights from the different LEDs to form a single color, the perception of which is dictated by the relative intensities of the individual colored LEDs. In other embodiments, no diffuser at all may be used, in order to allow a user to simultaneously perceive multiple colors of the different LEDs. Also, when insect control is an issue, the lighting effects may be programmed to attract or repel insects, using conventionally known lighting techniques for the same.

Preferably, white LEDs 15 provide a primary source of illumination for the bulb 10. Alternatively (or in addition), the red, green, and blue LEDs 14a-14c may be configured to, in combination, produce white light, when their respective wavelengths are mixed by a diffuser or the like. A conventional light source, such as halogen or fluorescent light may also be used, in lieu of (or in addition to) the white and/or colored LEDs, as a primary light source. In the embodiment shown in FIG. 1, a compact fluorescent bulb 30 is disposed coupled to the base 24 in the housing 12, and provides an additional source of illumination. Alternatively, when the fluorescent bulb 30 is used, the while LEDs 15 may be omitted.

Power is also preferably provided to fragrance dispenser 20, which, in this embodiment, comprises a heater 18. It should be noted, however, that any one of a number of fragrance dispensers may be used. For exemplary purposes, we discuss our invention with respect to heat-assisted evaporation devices in which heat is applied to increase the evaporation rate of a fragrance oil, gel, or the like containing an active ingredient. In other embodiments, fan-assisted evaporation devices, piezo-electrically actuated atomization devices, and/or unassisted fragrance dispensers may be substituted. Unassisted fragrance dispensers may simply include venting mechanisms that expose the fragrance to the ambient environment, or other such designs that enhance/provide convective airflow across a fragrance delivery medium. Of course, if unassisted fragrance dispensers are used, power need not be provided to the fragrance dispenser. These alternative devices are known in the art, and will not be described in detail herein. Also, other than a fragrance, other active ingredients may be used, such as air sanitizers and insect control substances (e.g., an insecticide or insect attractant).

Preferably, heater 18 includes a metal oxide resistor or wire wound resistor potted in a ceramic block. Of course, other heating devices may be used for the heater 18, such as a PTC (Positive Temperature Coefficient) heater, a coil resistance heater, printed circuitry, an etched foil heating device, or the like. When in use, heater 18 generates heat for heating the active ingredient of liquid or gel formulations stored in a fragrance cartridge 22. Such arrangements of heat-assisted evaporation devices are known in the art, and will not be described in detail herein. In general, however, cartridge 22 contains a formulation/active ingredient whose evaporation rate increases with the application of heat, thus allowing the evaporation rate (and consequently, the potency) to be controlled as the heat is varied.

Preferably, a compartment 23 is provided to receive the fragrance cartridge 22, which is replaceable in this embodiment. Any one of a number of known mounting mechanisms may be used to removably secure the cartridge 22 in the compartment 23, but preferably, the cartridge slides into compartment 23, so as to become wedged therein, or snaps into place using a system of mating protrusions and recesses. This allows the user to easily remove and replace spent cartridges, such as reservoirs containing fragrance oils, with the oils being communicated from the reservoir to the ambient environment with or without a porous wick, or gel cartridges which, when mounted, expose a gel impregnated with fragrance to the ambient environment.

Switch 26 is provided on base 24, to allow a user to control the operation of bulb 10. Although a switch is shown herein for exemplary purposes, any one of a number of user interfaces may be used so that the user may adjust the setting of the bulb 10. Such adjustments can include changing the color of the light emitted from the LEDs 14a-14c and 15, adjusting the brightness of the LEDs, switching between white light, colored light, and off settings, adjusting the evaporation rate of the fragrance (e.g., by adjusting the heat level, when a heat assisted device is used), and/or setting predetermined programs for light shows or fragrance emission changes that may be stored in a memory and operated by a processor (as discussed in more detail below). In preferred embodiments, the user interface is a button or switch that may be toggled to change the operation of the bulb 10 between different predetermined settings. In other embodiments, more than one button or switch may be provided to provide enhanced control by the user. For example, some suitable user interfaces are described in International Publication No. WO2005/003625.

Figure 2:
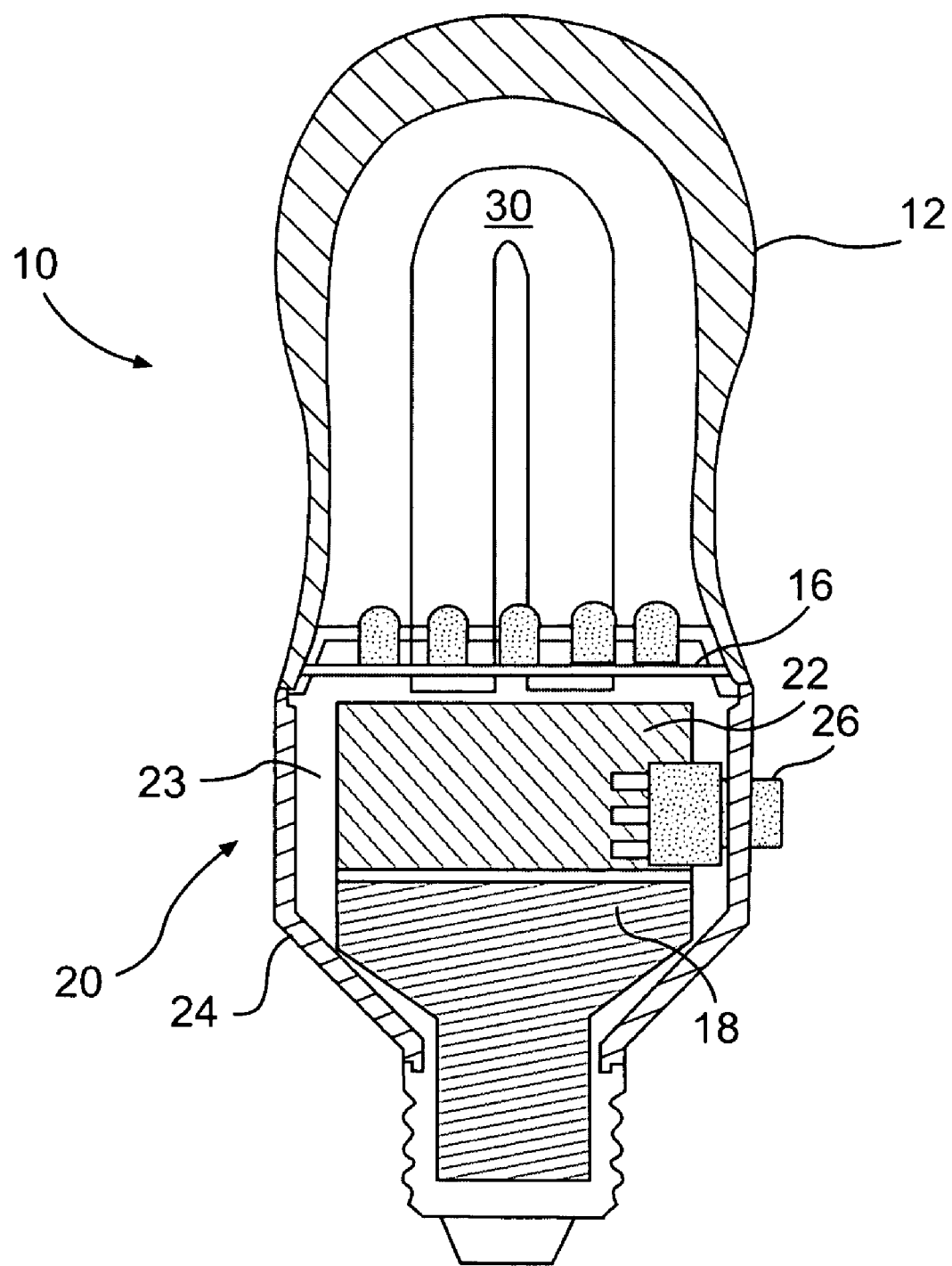
FIG. 2 is a cross-sectional view of another bulb according to our invention with a threaded, screw-in base.

FIG. 2 shows another embodiment of our invention in which the arrangement of the compartment 23 and heater 18 is altered. The remaining features are the same as those shown in FIG. 1, and a description thereof will not be repeated.

Figure 3:
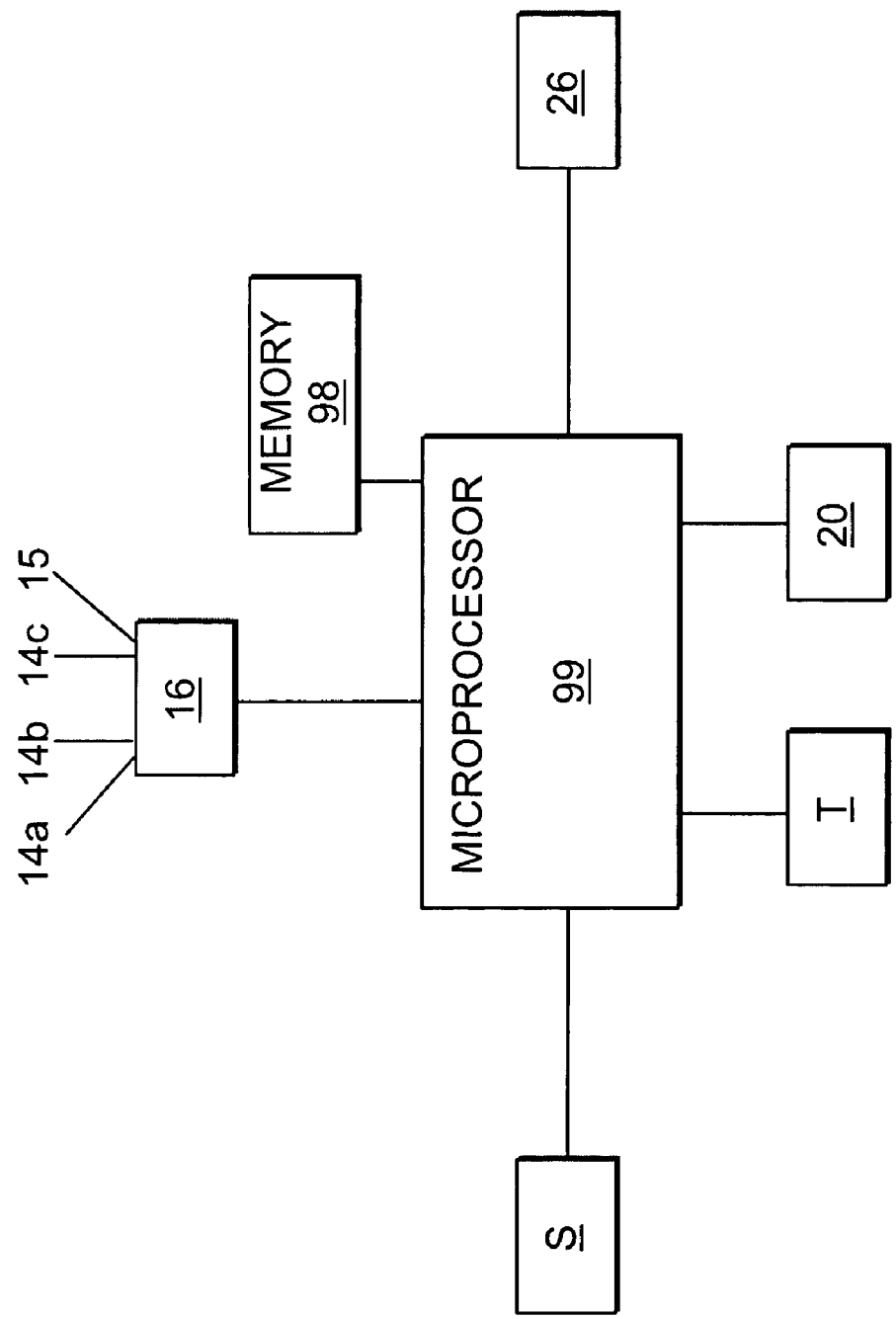
FIG. 3 is a schematic diagram of functional units of a bulb according to our invention.

FIG. 3 shows a diagrammatic representation of functional units of a preferred bulb 10. Microcontroller 99 is a programmable controller that produces output signals to control the emission of light from the LEDs of light array 16, and the amount of fragrance emitted from fragrance dispenser 20. Alternatively, one or more of the control features may be mechanically set by a user, without the assistance of a microprocessor. Such basic controls would be readily understood by one of ordinary skill in the art. Preferably, however, microcontroller 99 produces and outputs the signals to operate these devices according to one or more programs stored in the memory 98. The signals may be in the form of voltages, coded pulses, or other signals, which control the operation of the components. The programs may be preset in the memory 98 and then selected and activated by a user through a user interface (e.g., switch 26). Alternatively, switch 26 may set the lighting condition without reference to a stored program. Operation of microcontroller 99 can also be activated to produce a presentation according to a signal from sensor S. Sensor S may include, for example, a motion sensor, a sound sensor, a timing sensor, an infrared sensor, a power source-monitoring sensor, or the like. If a power source-monitoring sensor is used, the microcontroller 99 may be configured to activate and/or change the presentation of light and/or fragrance when a power switch of a light socket or lamp in which the bulb is received is toggled (e.g., one toggle activates the fluorescent light source 30, two toggles in succession activates the LED array, etc.). Bulb 10 may also include a timing mechanism T. The timing mechanism T may be an oscillator, crystal, conventional clock, etc. The timing mechanism T may control the operation of microcontroller 99 in accordance with the program from the memory 98. In addition, the timing mechanism T may be used to control the length of a presentation of light, and/or aroma set by a program in memory 98, as programmed by a user.

Control Mechanisms

As discussed above, the components for emitting light and fragrance may be configured to work in coordination with each other in any one of a number of ways. Provided below are preferred embodiments for configuring and controlling our invention to emit light and fragrance. These are, however, only preferred embodiments, and numerous other configurations are possible.

Figure 4:
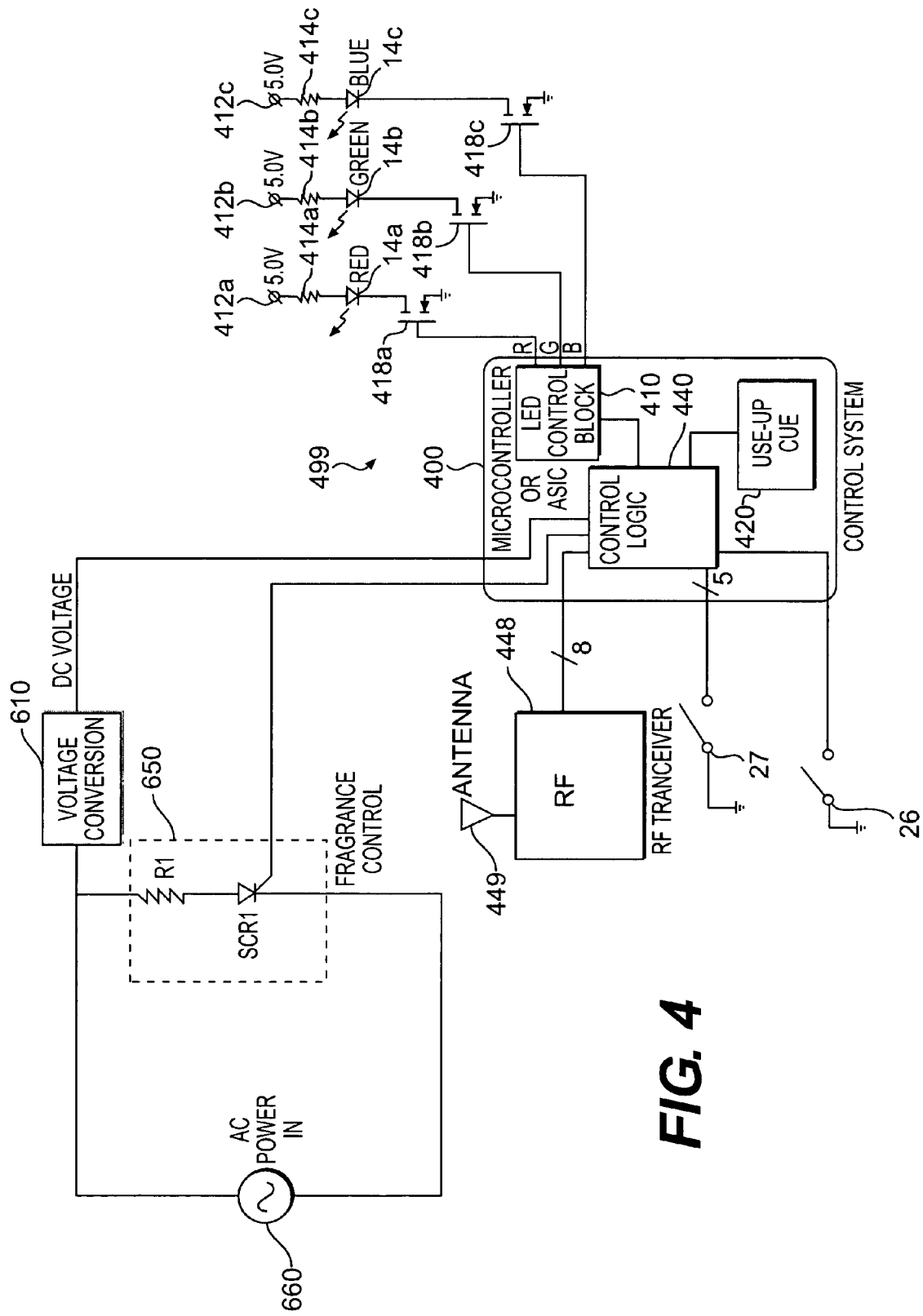
FIG. 4 is a circuit diagram of the control mechanisms for a bulb according to our invention.

FIG. 4 shows a circuit diagram for one control arrangement for operating bulb 10 that produces a coordinated/combined presentation of light and fragrance. A microcontroller (or ASIC) 400 controls the operation of the bulb 10. Power is supplied to the system 499 through a lamp (AC power source 660). A voltage conversion device 610 converts the AC voltage from the AC power source 660 to a DC voltage. A microprocessor 400 receives power from voltage conversion device 610 and controls the operation of system 499 using the received power.

Microcontroller 400 includes a control logic 440 that provides the operational instructions to the various elements of the bulb 10 in accordance with input signals or internal programs. The control logic 440 converts received signals or runs internal software routines to set the operation of the array of LEDs 14*a-c* and/or the fragrance control system 650 (e.g., fragrance dispenser 20), with a resistor R1 acting as the heater.

The control logic 440 sends a signal for controlling the operation of the array of LEDs to LED control block 410. When using pulse width modulation to drive and control the LED array, the LED control block 410 sets the duty cycles for the LEDs based on the instruction from the control logic 440.

Supply lines 412*a*-412*c* supply voltage across resistors 414*a*-414*c*, from power supply 404. Preferably, the voltage supplied across resistors 414*a*-414*c* is between about 3.5 and about 5.0 volts. Resistors 414*a*-414*c* in turn power a red LED 14*a*, a green LED 14*b*, and a blue LED 14*c*, respectively. Field effect transistors (FETs) 418*a*-418*c* are turned on and off in accordance with the respective duty cycles generated by the LED control block 410. Operation of the FETs 418*a*-418*c* control the LEDs 14*a*-14*c* to be activated for the portions of the duty cycle set by the LED control block 410. Thus, the intensity and color of the light emitted from the LEDs 14*a*-14*c* can be varied to produce the desired effects. Typically, pulse width modulation is used to control a constant current to be applied to a given diode for a set period of one duty cycle, thus controlling the total current applied to the LED over the full duty cycle. Thus, the diode flickers on for the set portion of each duty cycle, and off for the remainder of the duty cycle. Of course, this on and off operation is so fast (a typical duty cycle is in the range of a few milliseconds) that the intensity of the diode appears constant to an observer (with no discernable flicker), until the set period of activation over the duty cycle is changed.

The intensity and exact color of the light emitted from the housing of the bulb 10 may be varied by changing the current applied to each diode. The different combinations of LED operations will alter the perceived color when the light from the LEDs is diffused to form one perceived color.

While three LEDs are shown with respect to this embodiment, any number of LEDs may be used. In addition, the choice of which color LEDs to provide may be dictated by design preferences.

When three colors of LEDs are used, typically, mixtures of red, green, and blue LEDs are preferred. Generally, one of each color LED will be provided in close proximity to one of each other color. With such an arrangement, the exact color of each diode of the set of three different colors can be adjusted to create a blended color, for example, amber or purple. This blending can be achieved by providing the three diodes in such close proximity that the observer only sees the blend of colored lights, rather than each individual diode. Alternatively, or in addition, a diffuser may be provided to diffuse the light of the three diodes to produce the combined color. In other embodiments, the lights may be projected off of a surface to be combined before being viewed by an observer. When the LEDs are not placed close to each other, or there is not sufficient diffusion, multiple colors may be perceived in the bulb 10. This is a matter of design preference.

LEDs of a wide array of colors are readily available from lighting manufactures. Also, the arrangement and operation of LEDs to achieve a desired presentation would be apparent to one of ordinary skill.

White LEDs 15 and/or fluorescent bulb 30 may also be connected to control block 410, or may be controlled through separate means, inasmuch as the white LED(s) (or other conventional white light source) is typically either on or off and is not necessarily subject to the same range of control (unless dimmers or the like are used). Such modifications, however, would be readily understood by one of ordinary skill in the art.

The microprocessor 400 may also send a control signal to fragrance control 650, as shown in FIG. 4. In this embodiment, the fragrance dispenser being controlled is an evaporative-type dispenser. A resistor R1 is heated by a current passing across the resistor R1. Typically, the resistor R1 is placed adjacent to an area at which a fragrance-containing gel or oil is exposed to air and the heat from the resistor R1 causes the fragrance to be vaporized. A switch SCR1 varies the current passing across the resistor R1, thus varying the heat produced by resistor R1 and the rate of vaporization of the fragrance. In alternative embodiments, the resistor R1 may be replaced and/or supplemented by a fan which is controlled by switch SCR1, or an atomization device. Also, switch SCR1 may be replaced by an FET in other embodiments. Further, the fragrance dispenser may also be mechanically adjusted by a user, rather than through a microprocessor.

Microprocessor 400 may also control a use-up cue 420. The use-up cue 420 tracks the use of fragrance control to estimate the time at which the fragrance in the fragrance dispenser is likely to be used up. When the use-up cue 420 determines that fragrance has been spent, it sends a signal to LED control block 410 to cause the LEDs to illuminate in a pattern, color, or other manner to indicate to a user that it is time to refill or replace a fragrance in the fragrance dispenser.

The control logic 440 may be programmed/controlled in any number of ways. In one embodiment, an RF transceiver 448 receives an external signal, through an antenna 449, from a remote control. That signal is transmitted from the RF transceiver 448 to control logic 440 to set the presentation of light through the LED control block 410 and the fragrance control 650. Also, the operation of the control logic may be set by an internal program.

Alternatively, a user may manually set the fragrance output and light show. In this case, a program select switch 26 may be operated by a user to set a light show program for the LEDs 14a-14c. In this embodiment, switch 27 is also provided to control a fragrance level to be dispensed. Of course, additional buttons or switches may be provided, depending on the level of the control and programmability desired. In particular, a switch can be provided to control whether manual or automatic operation/programming is desired.

Figure 5:
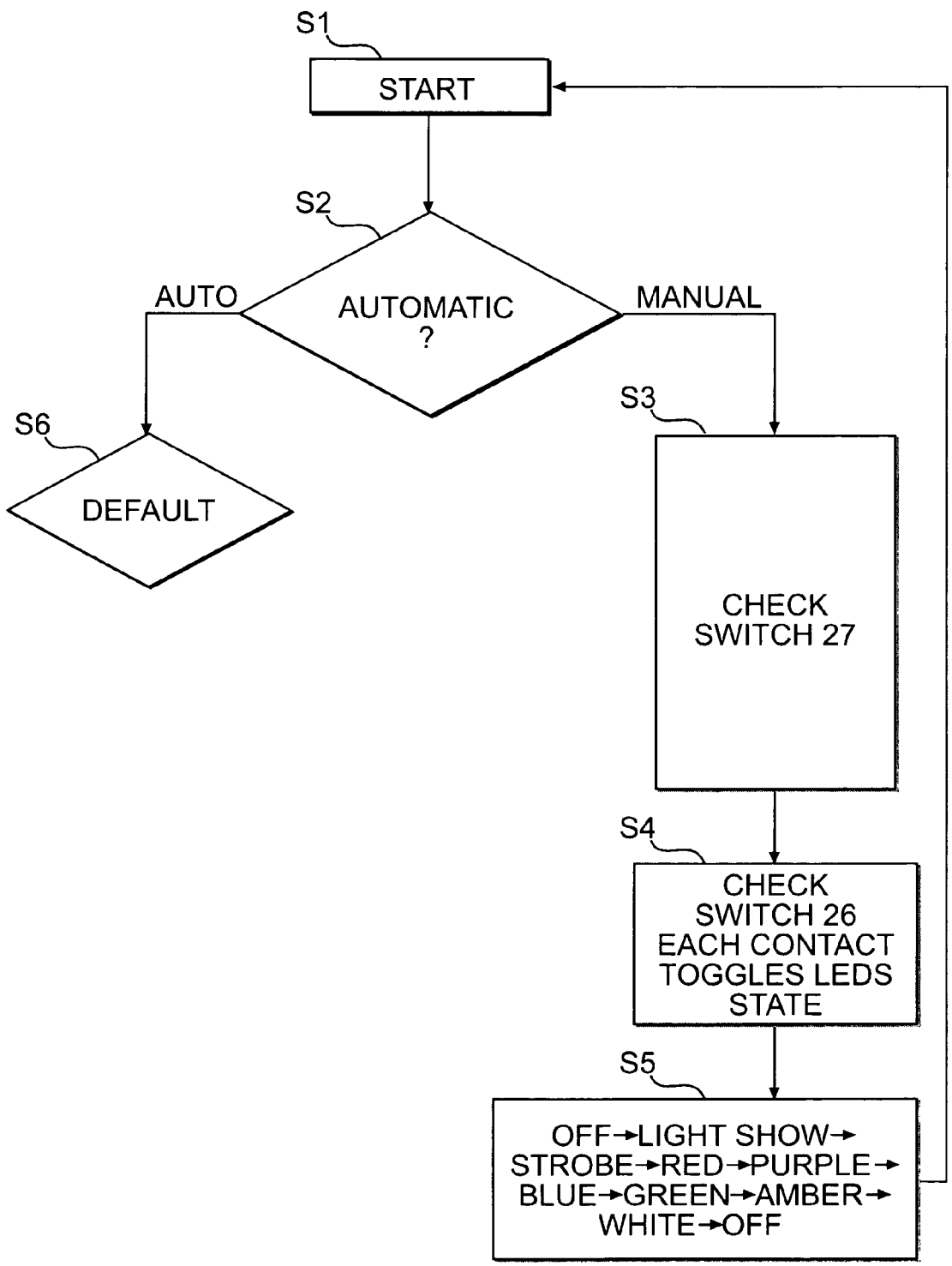
FIG. 5 is a flow chart of a program for operating a bulb according to our invention.

FIG. 5 shows one program for operating the control system shown in FIG. 4. One of ordinary skill in the art will appreciate that a wide variety of other programs may also be implemented to produce the desired control over the presentation of coordinated light and aroma.

The program starts operation of the device at step S1. At step S2, it is determined whether operation of the microntroller 400 is to be set manually by a user or automatically with a particular program. If manual operation is selected, the program proceeds to step S3. In step S3, the setting of the switch 27 is checked to set the level for operating the heater 18. For instance, in a first switch setting, the heater 18 is operated at a first temperature, while other temperatures may be set by other settings. In step S4, the operation of the switch 26 is checked. The system is set such that different preprogrammed light shows are selected depending on how many times a user toggles the switch 26. Step S5 sets the light show from among an off setting, a variant light show, a strobe setting, emission of red light, emission of purple light, emission of blue light, emission of amber light, and emission of white light, depending on the toggling of switch 26.

If the automatic mode is set in step S2, the program proceeds to step S6, in which a default setting is provided for operation. This automatic setting may be set by information from a program set in the memory, a sensor reading, a remote control, the power supply (e.g., by toggling a light switch controlling the lamp in which the bulb 10 is positioned), or the like.

These figures show only possible arrangements for configuring and controlling a device according to our invention. Many different embodiments may be constructed without departing from the spirit and scope of our invention. It should be understood that our invention is not limited to the specific embodiments described in this specification. To the contrary, our invention is intended to cover various modifications and equivalent arrangements included within the spirit and scope of our invention as defined by the claims. The scope of the claims is to be accorded the broadest interpretation so as to encompass all such modifications, equivalent structures and functions.

INDUSTRIAL APPLICABILITY

This invention makes it possible to achieve an overall desired effect by providing mood lighting and active ingredient emission, from a light bulb.

We claim:

1. A light bulb comprising:
a translucent housing comprising an open bottom;
the open bottom of the housing being connected to a base;
the base being connected to a connector for mating with a light socket, the base being disposed between the housing and the connector;
a plurality of LEDs positioned within the housing so as to emit light through the housing and the LEDs being supported by at least one of housing or the base;
an active ingredient dispenser disposed in the base, the active ingredient dispenser comprising a compartment for receiving and securing a replaceable active ingredient cartridge within the base, the active ingredient dispenser being capable of emitting an active ingredient from the cartridge and out the base when the cartridge is secured in the compartment.

2. The light bulb according to claim 1, wherein the plurality of LEDs include different color LEDs.

3. The light bulb according to claim 2, further comprising a controller for altering the color of light emitted through the housing by the plurality of LEDs.

4. The light bulb according to claim 2, further comprising a microprocessor for controlling the plurality of LEDs to emit light of different colors based on a user's input.

5. The light bulb according to claim 4, further comprising a memory for storing programs for operating the microprocessor to produce different predetermined lighting effects.

6. The light bulb according to claim 5, wherein at least one of the lighting effects includes automatically changing the color of light emitted from the housing over time.

7. The light bulb according to claim 5, further comprising an interface, which the user operates to change between the different programs stored in the memory.

8. The light bulb according to claim 2, wherein the housing comprises a non-fluorescent light diffuser.

9. The light bulb according to claim 1, wherein the compartment is configured to receive a cartridge in which the active ingredient is impregnated in a gel.

10. The light bulb according to claim 1, wherein the compartment is configured to receive a cartridge formed as a reservoir holding an oil containing the active ingredient.

11. The light bulb according to claim 1, wherein the dispenser is a heater that heats the active ingredient to facilitate evaporation of the active ingredient.

12. The light bulb according to claim 1, wherein the dispenser comprises a plurality of vents which facilitate airflow across the cartridge when the cartridge is mounted therein.

13. The light bulb according to claim 1, wherein the base has a threaded connector for mating with a threaded light socket.

14. The light bulb according to claim 1, wherein the base is configured to mate with a light socket for receiving one of an incandescent, a halogen, or a fluorescent light bulb.

15. The light bulb according to claim 1, wherein the active ingredient in the active ingredient cartridge is a fragrance.

16. The light bulb according to claim 1, wherein the active ingredient in the active ingredient cartridge is selected from the group consisting of a sanitizer, an insecticide, and an insect repellant.

17. The light bulb according to claim 1, further comprising a fluorescent light source positioned in the translucent housing.

18. A light bulb comprising:
a base disposed between a connector configured to mate with a light socket for receiving the light bulb and a translucent bulbous housing;
a plurality of LEDs, including LEDs of at least two different colors, coupled to the base and extending at least partially into the housing;

an active ingredient dispenser disposed in the base that dispenses an active ingredient from the light bulb when the active ingredient is provided therein; and a control mechanism, by which the light bulb can be controlled by a user to change at least one of a color of light emitted horn the housing by the plurality of LEDs, and an output rate of the active ingredient.

19. A light bulb according to claim 18, further comprising a fluorescent light source coupled to the base within the housing.

20. A light bulb according to claim 19, further comprising:

a control mechanism having a first setting that controls the fluorescent light source to produce substantially white light, and a second setting that controls the plurality of LEDs to produce colored light; and a user interface, by which a user can cause the control mechanism to switch between the first setting and the second setting.

* * * * *

UNITED STATES PATENT AND TRADEMARK OFFICE
CERTIFICATE OF CORRECTION

PATENT NO. : 7,246,919 B2  Page 1 of 1
APPLICATION NO. : 11/069964
DATED : July 24, 2007
INVENTOR(S) : Jose Porchia and Jeffrey J. Wolf It is certified that error appears in the above-identified patent and that said Letters Patent is hereby corrected as shown below:

Column 9: Line 6 Claim 18, replace "horn" with --from--

Signed and Sealed this

Fifth Day of August, 2008

JON W. DUDAS
*Director of the United States Patent and Trademark Office*